United States Patent [19]
Chance

[11] Patent Number: 5,167,230
[45] Date of Patent: Dec. 1, 1992

[54] USER-WEARABLE HEMOGLOBINOMETER FOR MEASURING THE METABOLIC CONDITION OF A SUBJECT

[75] Inventor: Britton Chance, Philadelphia, Pa.

[73] Assignee: NIM, Inc., Philadelphia, Pa.

[21] Appl. No.: 611,400

[22] Filed: Nov. 7, 1990

Related U.S. Application Data

[63] Continuation of Ser. No. 266,019, Nov. 2, 1988.

[51] Int. Cl.$^5$ ............................................. A61B 5/00
[52] U.S. Cl. ..................... 128/633; 128/664; 128/666; 356/41
[58] Field of Search ........ 128/634, 635, 637, 664–666; 356/39–41

[56] References Cited

U.S. PATENT DOCUMENTS

| | | | |
|---|---|---|---|
| 2,706,927 | 4/1955 | Wood | 88/14 |
| 3,068,742 | 12/1962 | Hicks, Jr. et al. | 88/14 |
| 3,412,729 | 11/1968 | Smith, Jr. | 128/2.05 |
| 3,461,856 | 8/1969 | Polyani | 128/2 |
| 3,638,640 | 2/1972 | Shaw | 128/2 R |
| 3,704,706 | 12/1972 | Herczfeld et al. | 128/2 R |
| 3,709,612 | 1/1973 | Clemens | 356/178 |
| 3,866,599 | 2/1975 | Johnson | 128/2 L |
| 3,998,550 | 12/1976 | Konishi et al. | 356/39 |
| 4,086,915 | 5/1978 | Kofsky et al. | 128/633 |
| 4,119,406 | 10/1978 | Clemens | 422/81 |
| 4,223,680 | 9/1980 | Jöbsis | 128/633 |
| 4,266,554 | 5/1981 | Hamaguri | 128/633 |
| 4,281,645 | 8/1981 | Jöbsis | 128/633 |
| 4,321,930 | 3/1982 | Jöbsis et al. | 128/633 |
| 4,380,240 | 4/1983 | Jöbsis et al. | 128/633 |
| 4,416,285 | 11/1983 | Shaw et al. | 128/634 |
| 4,576,173 | 3/1986 | Parker et al. | 128/664 |
| 4,773,422 | 9/1988 | Isaacson et al. | 128/665 |
| 4,774,679 | 9/1988 | Carlin | 364/550 |
| 4,805,623 | 2/1989 | Jöbsis | 128/633 |

FOREIGN PATENT DOCUMENTS

| | | | |
|---|---|---|---|
| 102816 | 3/1984 | European Pat. Off. | 128/633 |
| 0196396 | 10/1986 | European Pat. Off. | |
| 0282234 | 12/1987 | European Pat. Off. | |
| 2538985 | 5/1976 | Fed. Rep. of Germany | 128/633 |

*Primary Examiner*—David M. Shay
*Attorney, Agent, or Firm*—Fish & Richardson

[57] ABSTRACT

A system for non-invasively determining the oxygenation state of tissue located beneath the surface of the skin, such as muscle tissue, of an exercising person or other subject is disclosed. In a preferred embodiment, a user-wearable detector array and related circuitry which use near-infrared radiation to collect oxygenation data are provided. The apparatus also includes displays for displaying information regarding the oxygenation state in several ways. In one embodiment a user wearable wristband indicator connected to the detector array which is located at another location, such as on the leg, and provides information directly to the user. In another embodiment, a telemetry device allows remote monitoring of a subject during an activity, the oxygenation information being displayed to a coach or other observer. A separate, user-wearable battery pack, which is preferably designed to provide power for the duration of the activity being monitored, is also provided.

2 Claims, 2 Drawing Sheets

USER-WEARABLE HEMOGLOBINOMETER FOR MEASURING THE METABOLIC CONDITION OF A SUBJECT

This is a continuation of application Ser. No. 266,019, filed Nov. 2, 1988.

CROSS-REFERENCE TO RELATED APPLICATIONS

This application is related to copending application Ser. No. 266,116, filed Nov. 2, 1988, now abandoned, and Ser. No. 583,006, filed Sep. 17, 1990, now abandoned a continuation thereof in the name of Britton Chance, entitled, "Optical Coupling System For Use in Monitoring Oxygenation State Within Living Tissue", which is hereby incorporated by reference as if fully set forth herein.

BACKGROUND OF THE INVENTION

The present invention relates to wearable apparatus for noninvasive determinations of the concentration of oxygen in a specific target region of tissue. More specifically, the present invention discloses a user-wearable system for monitoring the oxygen concentration in the tissue of a subject undergoing aerobic stress, such as an exercising person.

The increasing popularity of all forms of exercise over the last several decades has also lead to an increased interest in the measurement of individual athletic performance. However, at the present time, athletes are limited to obtaining heartbeat and blood pressure data while they are exercising. Although of some use, these data do not reflect peripheral circulatory capacity or the oxygenation state of specific muscle tissue.

In order to measure oxygen delivery to the capillary bed of the muscles, an athlete must be tethered to electrocardiogram apparatus and have blood samples drawn while running on a treadmill. These are essentially operating room apparatus and procedures, which do not simulate the actual conditions of exercise. The measurement of aerobic efficiency by analyzing the oxygenation state of a particular muscle while exercising is important to a variety of persons. For example, as a casual jogger strives to become a marathon runner, the efficiency at which they use oxygen can severely impact performance; data reflecting the utilization of oxygen can provide information which allows an athlete to change pacing strategies or otherwise adjust their activity to produce better results. Other athletes, such as swimmers, cyclists and rowers would also find this information useful for evaluating performance. However, the use of blood oxygenation data is not limited to competitive athletes; even geriatrics who undergo mild aerobic exercise to maintain and improve their health ca benefit from data concerning the changes in blood oxygenation brought about by exercise or other activity. Other animals, such as racehorses, can also benefit form this type of performance data. By measuring the oxygen delivery to the muscles, both the quality of training and the natural ability to exercise may be evaluated.

In addition to monitoring and maximizing athletic performance, information pertaining to the delivery of oxygen to the limbs and the brain is important in military and space applications where changes in gravity and other stresses may result in fatigue, and ultimately, blackouts.

Although apparatus are available which measure the oxygenation content of blood using data collected from a fingertip or ear lobe, these devices do not actually measure the oxygenation state of nearby muscle groups or the brain. To monitor athletic performance, or the condition of exerted muscles, data collection must be performed at the site of interest. For example, runners will wish to know the condition of the muscles in their legs, and further wish to be provided with this information during a race, not in a laboratory. Therefore, for an apparatus measuring the metabolic condition of an athlete to be truly useful, a rugged, lightweight, user-wearable system must be provided.

One method by which the oxygen level in a muscle may be measured by tissue spectrometry. For example, red and near-red light, having wavelengths between about 600–800 nanometers (nm), will harmlessly penetrate body tissues. As the light penetrates the tissue, it migrates and is absorbed by deoxygenated hemoglobin in small blood vessels. Normally, tissue receives oxygen from hemoglobin contained in red blood cells, which circulate in the major blood vessels and eventually into the capillary bed, supplying muscle tissue with oxygen. Aerobic activity can cause the level of oxygen use to rise, causing a commensurate rise in the level of deoxyhemoglobin which is compensated for by increased blood flow in trained individuals. Near-red light is absorbed by tissue that is not receiving as much oxygen as the surrounding tissue due to increased levels of deoxyhemoglobin in less trained individuals. Thus, by determining the amount of incident radiation absorbed, the oxygenation state of a specific area of tissue, and the training level of an individual, can be determined.

SUMMARY OF THE INVENTION

The present invention provides a novel, wearable system for determining the metabolic condition of an aerobically stressed portion of the muscle tissue of an exercising person. The system comprises a lightweight rugged detector, worn against the skin surface of the subject, adjacent the muscle being monitored. The system of the present invention thus minimizes any performance impairment. The preferred system further comprises a wearable power pack and a wearable display means for displaying information indicative of the aerobic metabolic condition of the region being monitored. In a preferred embodiment intended for use while running or engaged in similar athletic activities, the display is a worn on the wrist and displays information from a leg-mounted detector. In another embodiment, intended to provide information to coaches, a telemetry system is employed to transmit a signal carrying the data from the detector to a remote location, for processing and display.

The detector of the present invention preferably employs a continuous wave spectrophotometer having one or more sources of electromagnetic radiation with wavelengths between about 760 nanometers and about 800 nanometers directed into the tissue of the subject. The detector is efficiently coupled to the body tissue and utilizes the principle of photon migration to detect the portion of the transmitted radiation arriving at an adjacent skin region.

The present invention also discloses methods for displaying the aerobic metabolic condition of a subject. The percentage of deoxyhemoglobin in the blood of the subject is determined, and a signal representative of this percentage is converted into a graphic representation. The display may preferably be a digital display, a bar graph or a series of deoxyhemoglobin levels placed on a time scale.

OBJECTS OF THE INVENTION

It is an object of the present invention to provide methods and apparatus which allow a rapid determination of the oxygenation state of tissue, such as muscle tissue, located beneath the surface of the skin of a subject, such as an athlete, without requiring the subject to be tethered or physically connected to laboratory or operating room monitoring equipment.

It is also an object of the present invention to provide apparatus which may be attached to a user which would determine the oxygenation state of a portion of the user's body and provide that information in a readily understandable form.

It is a further object of certain embodiments of the present invention to provide information pertaining to the oxygenation state of tissue directly to a user wearing the apparatus of the present invention.

It is another object of certain embodiments of the present invention to transmit information pertaining to the oxygenation state of tissue to a remote observer.

DETAILED DESCRIPTION

Figures 1, 1A, 1B:
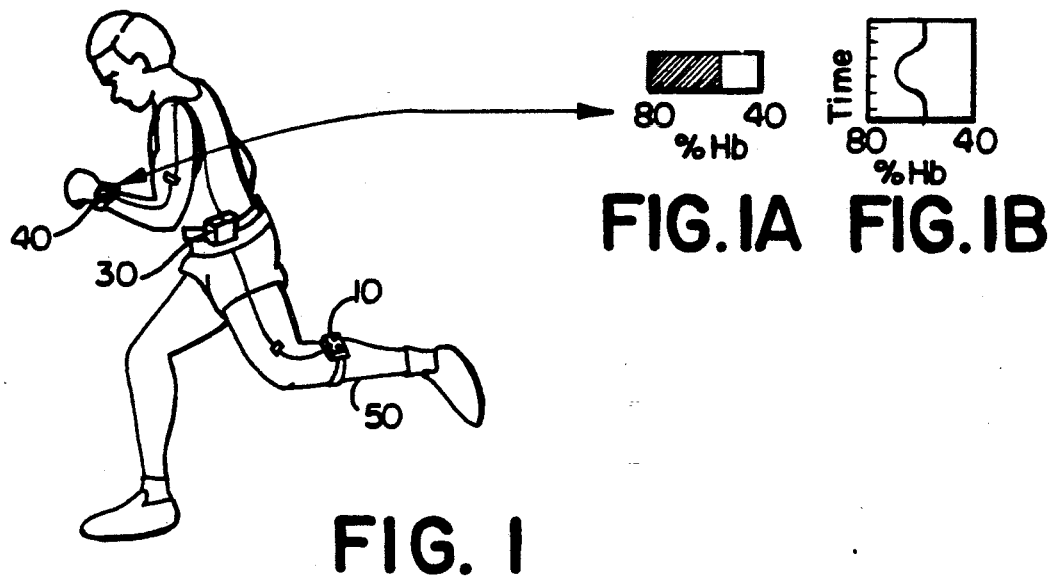
FIG. 1 is a depiction of a preferred configuration of an embodiment of the present invention.

A preferred embodiment of the apparatus of the present invention is illustrated in FIG. 1. In this embodiment an electro-optical pickoff detector unit 10 is worn on the leg of the exercising subject 50. It is preferred that the weight of the detector be kept to a minimum so that hindrance to a competing athlete is negligible. In a preferred embodiment, the detector will be housed in a flexible array constructed from a suitable non-irritating, lightweight material.

Power is provided to the detector unit 10 from a replaceable battery pack 30. The replaceable power pack 30 is preferably designed to be of minimal dimensions and weight. Most preferably, the battery pack 30 would be designed to last only for the duration of the activity, e.g., several minutes of sprinting, several hours for a marathon runner, etc. In competitive sports applications, the life of the battery pack is preferably based upon the interval between substitutions or other interruptions between periods of competition.

The embodiment illustrated in FIG. 1 further comprises an arm indicator 40, which is preferably worn on the arm in the manner of a wristwatch. The arm indicator 40 displays the percentage of deoxyhemoglobin (%Hb) as a measure of the subject's metabolic state. As seen in FIG. 1A, such a display may comprise a simple readout of this information, such as a bar graph. Alternatively, the information displayed may be placed on a time scale, to graphically illustrate the change in %Hb concentration over the course of the activity, as illustrated by FIG. 1B. In a most preferred embodiment, the graphic displays illustrated by FIGS. 1A and 1B are comprised of liquid crystal displays (LCD's), although other electrical or electronic display means may also be used. The amplitude interval of this embodiment is preferably divided into 6–10 levels, each covering a portion of the designated %Hb scale.

It will be appreciated that the range of the %Hb scale may be adjusted depending upon the range expected to occur during the activity. Since the precision of the present invention is limited by that of the indicator, the range which is displayed is an important variable parameter. In the most accurate embodiment of the present invention, with the endpoints of the %Hb scale set at 20% and 40%, the apparatus would have an accuracy of about 6%, which is about the limit of precision which can be obtained from a moving limb. One of ordinary skill will realize that the gain of the apparatus is preset, depending upon the intensity of the activity expected. In a most preferred embodiment, a button placed on the arm indicator 40 allows the gain to be set.

Figure 2:
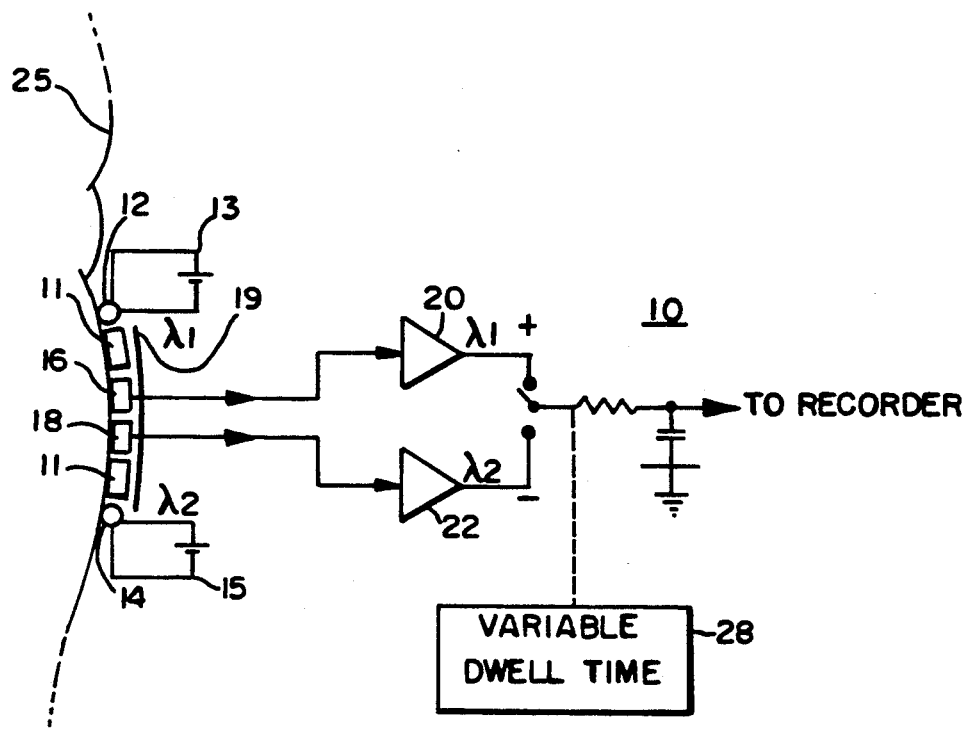
FIG. 2 is a partially diagrammatic, partially schematic representation of a preferred embodiment detector.

Referring now to FIG. 2, there is illustrated a partially schematic, partially diagrammatic representation of a preferred embodiment of a circuit which comprises the optical pickoff component of a DC tissue spectrophotometer detector 10 contemplated for use in the system of the present invention. The detector 10 is shown for illustrative purposes mounted against a skin surface 25 of a subject. In a typical configuration, the detector is mounted against either large, homogeneous muscles, such as the gastrocnemius or the quadriceps or against the forehead of an adult. Two lamps 12,14 and two detectors 16,18 are contained in a flexible waterproof array. Also contained in the array is an opaque specular barrier 11, which preferably comprises concentric rings of material between the lamps 12,14 and the detectors 16,18 which acts as a barrier zone to light of a specified wavelength. Most preferably, the material which comprises the barrier zone 11 will not only be opaque to light within a specified region, but will further act as an absorber as well. The configuration of dual wavelength light sources combined with a barrier zone is disclosed in "Optical Coupling System for Use in Monitoring Oxygenation State Within Living Tissue", application Ser. No. 266,116; filed Nov. 2, 1988; and application Ser. No. 583,006, filed Sep. 17, 1990, a continuation thereof, both of which are incorporated herein by reference.

Thus, superficial light rays from the skin are, in effect, blocked by the opaque barrier 11 from entering the detectors 16,18. This blocking action by the barrier 11 of these superficial rays enables the system to determine the oxygenation state of hemoglobin within the muscle rather than at the skin surface. The rays that migrate deep within the tissue are received by the detectors 16,18. The light rays that migrate superficially "escape" through the skin surface and will be absorbed by the opaque barrier 11. When, for example, a 760 nm impulse is applied, the deoxygenated hemoglobin (Hb) within the muscle is detected and when an 800 nm signal is applied, the oxygenated and deoxygenated hemoglobin ($HbO_2$ and Hb) within the tissue region are detected. The system is able to ignore the oxygenation state at the skin surface and determine that within the tissue.

The lamps 12,14 may be, for example, ½ W flashlight bulbs that are periodically illuminated in the NR region. The lamps are provided with cutoff filters so that only energy of a specified wavelength illuminates the tissue. The silicon diode detectors 16,18 are most preferably sensitive to 760±20 nm and 800±20 nm wavelengths respectively.

In a preferred embodiment, the lamps 12,14 are light emitting diode (LED) sources, which emit light having a wavelength of about 760 nanometers and about 800 nanometers respectively. In either embodiment, the lamps are flashed or pulsed at a predetermined repetition rate. The repetition rate of sampling, i.e., the rate at which the lamps are flashed determines the rate at which data may be collected. Thus, for a long distance runner, the lamps are flashed slowly; the output is commensurately changed for a sprinter, the lamps flashed rapidly to produce sufficient data to evaluate an exercise having a duration on the order of seconds. The selection of LEDs as sources of electromagnetic radiation provides a further advantage, since these sources produce a signal-to-noise ratio (S/N) approximately on order of magnitude greater than the optical coupling systems using optical light fiber sources disclosed in the co-pending patent applications referenced above.

Figure 4:
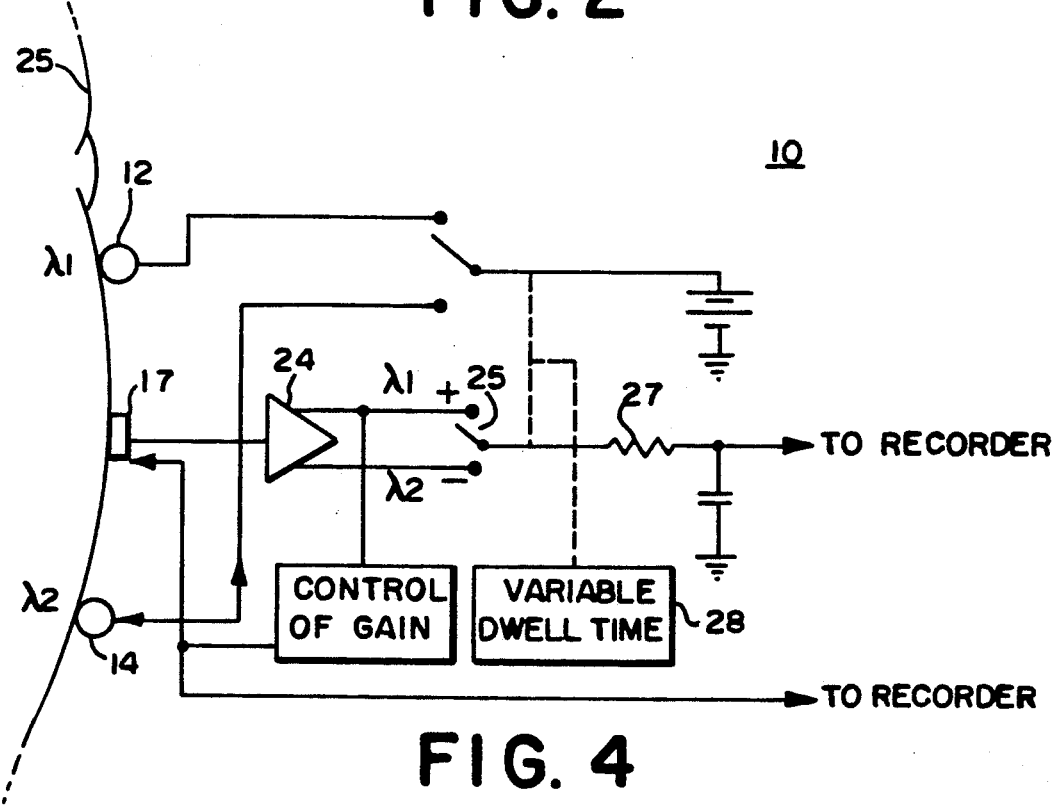
FIG. 4 is a partially diagrammatic, partial schematic representation of an alternate preferred embodiment detector.

Referring now to FIG. 4, an alternate embodiment of a circuit for use with the present invention is illustrated. In this case a single detector 17 responding to separate light flashes collects and transmits signals to an amplifier 24, which has bipolar outputs that are connected intermittently to an integrator 27 by a switch 25. Another switch 26 adjusts the relative duration of the two light pulses to equalize the two signals. One of ordinary skill will understand that those portions of FIG. 2 and FIG. 4 having the same reference numerals perform substantially similar functions. Many details of the particular circuits comprising the present invention need not be set forth with particularity as they are well known or will be obvious to those of ordinary skill.

Referring to FIG. 2, it can be seen that the detectors 16,18 are also protected by a transmitting filter 19 to minimize the effect of background light. The filter 19 may be comprised of a separate member, a coating or integrated into the housing of the circuit. The DC output of each of the detectors 16,18 is time-shared into its respective differential amplifier 20,22. The amplifiers are connected in opposite polarity, one non-inverting, the other inverting. The dwell time of the switch 23 connecting the amplifiers 20,22 is adjusted to equalize the response of the two signals by appropriate circuitry 28. The signal from the integrator is coupled to a recorder (not illustrated). As shown in FIG. 4, the signal from the 800 nm lamp 12 may be simultaneously employed to vary the gain of the amplifier 24 so as to correct the signals for changes of blood volume and to produce the ratio of the two signals, and thus maintaining constant sensitivity for difference detection. One of ordinary skill will appreciate that a similar gain compensation circuit can be incorporated into the circuitry of the 800 nm detector amplifier 22, shown in FIG. 2. Whether incorporated into the circuits of FIG. 2 or FIG. 4, the 800 nm signal is also coupled to a second recorder channel to collect data reflecting total absorbtion or blood volume.

Figure 3:
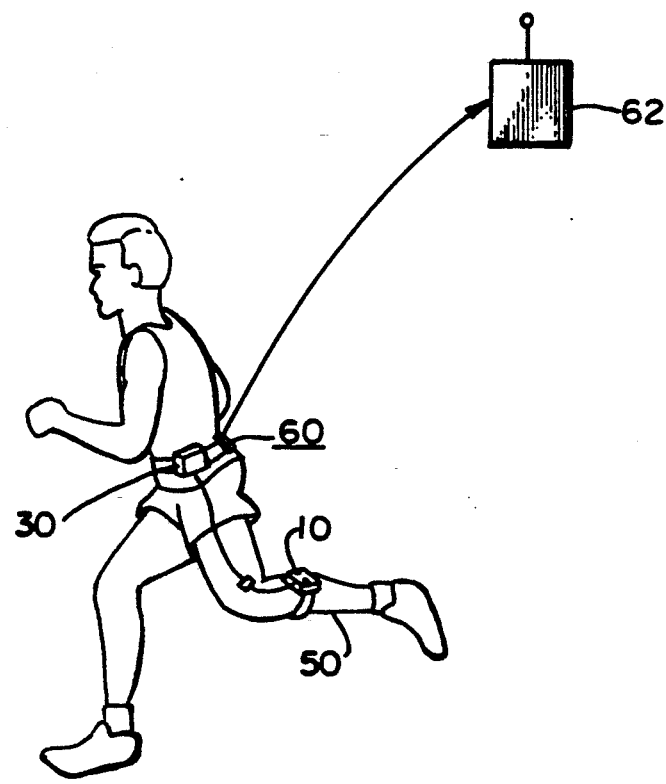
FIG. 3 illustrates another preferred configuration of an embodiment of the present invention.

Another configuration of the present invention is illustrated in FIG. 3. In this embodiment, a radio-linked telemetry system comprised of a transmitter 60 attached to the subject and a receiver 62, allows the remote monitoring of the subject. A supervisor, coach, or clinician is thereby enabled to monitor the performance of the subject. The data display is remote, one of ordinary skill will appreciate that the displays utilized may be similar to those illustrated in FIGS. 1A and 1B, or may be more complex, displaying data using various scales, time overlays, colors, etc. In a most preferred embodiment the telemetry signal would be carried on the 220-400 MHz band using a transmitter in the 100 MW range.

The configuration illustrated by FIG. 3 allows the present invention to monitor athletes in competition or workers and military/space personnel located in remote locations. For example, the apparatus of the present invention may be used in training to determine the duration of peak performance and the appropriate times for the substitution of fresh players or other adjustments. This configuration would also be preferred for monitoring the metabolic condition of an animal such as a racehorse, racing dog, or any animal whose metabolic condition is being studied for clinical or other purposes.

In any of the embodiments of the present invention, it is preferred that the data be integrated over at least about ten seconds to smooth out irregularities which normally occur in the concentration of dexyhemoglobin during exercise. However, it will be understood that the period integration can be varied, depending upon the duration of the activity being monitored.

Although manual balancing of the apparatus of the present invention is required, in a preferred embodiment, the balancing is accomplished by depressing a button, which will normalize the output of the two wavelengths.

One of ordinary skill in the art will appreciate that the present invention is not limited to the particular embodiments described in detail. Modifications to the circuitry disclosed, and other aspects of the spectrophotometer configurations disclosed, as well as other modifications to the physical arrangement of the present apparatus will be obvious to those of ordinary skill. Further, the present invention is not limited to any of the uses described herein. In order to fully appreciate the scope of the present invention, reference should be made to the following claims.

What is claimed is:

1. A method of collecting data indicative of the concentration of deoxyhemoglobin within a target region of the tissue of a subject, said tissue having an exterior surface, comprising the steps of:
   (a) providing wearable tissue oximetry apparatus comprising:
      (i) a detector means worn by said subject for producing a signal proportional to the deoxyhemoglobin concentration of a target area of the tissue said signal comprising a baseline portion and a pulsatile portion, said detector means being removably attached against the exterior surface of said target area;
      (ii) power pack means worn by said subject for delivering current electrically connected to said detector means; and
      (iii) display means for displaying information indicative of the concentration of deoxyhemoglobin within said target area;
   (b) activating said detector means by flashing at least two sources of electromagnetic radiation which are directed into said target area;
   (c) detecting the scattered portion of the electromagnetic radiation which has migrated through the target area and producing said signal;
   (d) determining data indicative of the concentration of deoxyhemoglobin in the target area by processing the baseline portion of the signal; and
   (e) displaying the data indicative of the concentration of deoxyhemoglobin in said target area.

2. The method of claim 1, wherein said display is created upon demand.

* * * * *